(12) United States Patent
Mallory

(10) Patent No.: US 6,503,281 B1
(45) Date of Patent: Jan. 7, 2003

(54) TOTAL HIP REPLACEMENT

(76) Inventor: Thomas H. Mallory, 720 E. Broad St., Columbus, OH (US) 43215

( * ) Notice: Subject to any disclaimer, the term of this patent is extended or adjusted under 35 U.S.C. 154(b) by 0 days.

(21) Appl. No.: 09/648,493

(22) Filed: Aug. 25, 2000

(51) Int. Cl.$^7$ ................................................. A61F 2/32
(52) U.S. Cl. .................. 623/22.15; 623/22.11
(58) Field of Search ........................... 623/22.11–22.39

(56) References Cited

U.S. PATENT DOCUMENTS

| | | | |
|---|---|---|---|
| 3,521,302 A | 7/1970 | Muller .................. | 3/1 |
| 3,554,193 A | 1/1971 | Konstantinou et al. ....... | 128/92 |
| 3,824,995 A * | 7/1974 | Getscher et al. ............. | 128/92 |
| 3,925,824 A | 12/1975 | Freeman et al .............. | 3/1.912 |
| 4,001,897 A | 1/1977 | Rambert et al. ............. | 3/1.913 |
| 4,035,848 A | 7/1977 | Wagner ...................... | 3/1.913 |
| 4,274,164 A | 6/1981 | Rehder et al. ............... | 3/1.913 |
| 4,332,036 A | 6/1982 | Sutter et al. .................. | 3/1.91 |
| 4,532,661 A | 8/1985 | Halpern ...................... | 623/23 |
| 4,650,491 A | 3/1987 | Parchinski .................... | 623/22 |
| 4,676,799 A | 6/1987 | Legrand ..................... | 623/22 |
| 4,770,659 A | 9/1988 | Kendall ....................... | 623/22 |
| 4,792,337 A | 12/1988 | Muller ....................... | 623/22 |
| 4,871,368 A | 10/1989 | Wagner ...................... | 623/22 |
| 4,963,154 A | 10/1990 | Anapliotis et al. ............ | 623/22 |
| 5,041,140 A | 8/1991 | Teinturier .................... | 623/22 |
| 5,057,111 A | 10/1991 | Park ........................... | 606/69 |
| 5,092,898 A | 3/1992 | Bekki et al. .................. | 623/22 |
| 5,133,766 A | 7/1992 | Halpern ...................... | 623/23 |
| 5,201,771 A | 4/1993 | Belykh et al. ................ | 623/23 |
| 5,358,532 A | 10/1994 | Evans et al. .................. | 623/22 |
| 5,376,122 A * | 12/1994 | Pappas et al. ................ | 623/22 |
| 5,496,373 A | 3/1996 | Schmidt ...................... | 623/16 |
| 5,725,593 A | 3/1998 | Caracciolo ................... | 623/22 |

* cited by examiner

Primary Examiner—Corrine McDermott
Assistant Examiner—Thomas C. Barrett
(74) Attorney, Agent, or Firm—Standley & Gilcrest LLP

(57) ABSTRACT

A hip assembly and method are described in which a femoral head cap component secured to the femur with at least one screw is engaged with an acetabulum shell component affixed to the acetabulum with at least one screw, and a trochanteric osteotomy plate is secured to the femur with screws. The assembly further includes a psoas recess in the acetabulum shell for allowing freedom of movement of the illiopsoas tendon, countersunk cancellous screws for securing the components to the bones, and fins mounted on the femoral cap to prevent rotation in the bone.

4 Claims, 6 Drawing Sheets

TOTAL HIP REPLACEMENT

BACKGROUND AND SUMMARY OF THE INVENTION

The present invention relates generally to the medical field of orthopedics, and more particularly, to an apparatus and medical procedure for total hip replacement. Artificial joints have been used for many years to replace human joints that have suffered severe injury or the negative effects of aging through arthritis or other maladies. The goal of artificial joints is to provide the user with the same benefits of the natural joint without the pain or restriction of movement that the user was experiencing from the old, natural joint.

The procedure of hip replacement is well documented. The present invention comprises many improvements to known hip replacement apparatus and procedures. An exemplary embodiment of the present invention includes: a trochanteric osteotomy plate, preferably in "Y" shape; a femoral hemispheral dome or cap component, preferably press fit, with a porous under surface, and one or more dome apertures for insertion of countersunk cancellous screw(s) in retrograde position; an acetabural hemispheral metal shell component preferably with a psoas recess (to avoid interference with the illio-psoas tendon), and with screw apertures clustered for cancellous screw fixation in a countersunk installation; and, tri-finned fixation between the dome component and the shell component to prevent rotation there between.

This and other features, as well as the advantages of the total anatomic hip prosthesis according to the present invention, are more particularly shown in the following detailed description of an exemplary embodiment of the present invention with reference to the following figures:

DETAILED DESCRIPTION OF THE PREFERRED EMBODIMENT

Figure 1:
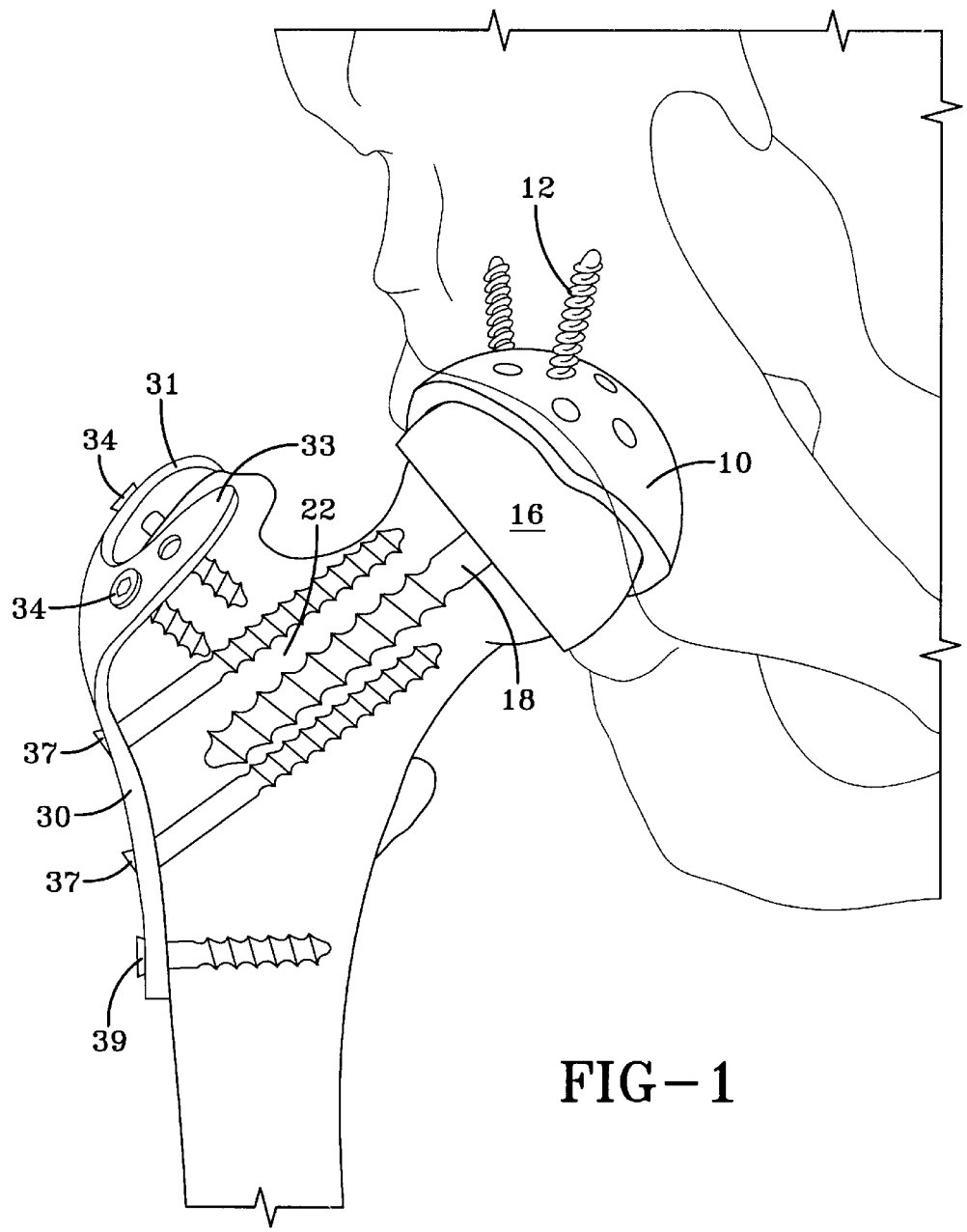
FIG. 1 is an elevation view of the total hip prosthesis according to a preferred embodiment of the present invention, (as it would be visible by x-ray through bone)

Referring now to the drawings, there is shown in FIGS. 1–6 exemplary embodiments of the total anatomic hip prosthesis of the present invention. The invention includes an acetabulum shell 10, one or more fasteners 12 for securing the acetabulum shell in the iliac fossa 14. Also shown is a femoral cap 16 secured by one or more fasteners 18 to the femoral head 20. On the other side of the higher epiphysis 22 there is the end of the diaphysis 23 under the great trochanter 24. A trochanteric osteotomy plate 30 in the shape of a "Y" hooks over the top of the greater trochanteric bone fragment 24 and then plates down along the lateral shaft of the femur 32 with fasteners 34 that pass through each branch 31, 33 of the "Y" and continue past the osteotomy and into the neck of the femur and fasteners 37 on each side of the resurfacing head screw, and optional fastener 39 at the base of the plate 30.

While the order of installation of the components may vary, a preferred order for carrying out the procedure of total hip replacement is as follows: The cap 16 is placed on the femoral head 20 through a fastener(s) 18 placed in a suitable depression of the cap. The trochanteric osteotomy plate 30 is affixed over the great trochanter with fasteners 34, 37, 39. The prosthetic acetabulum shell 10 may be inserted in the iliac fossa 14 before or after the above steps. The cap 16 is then pressed into the acetabulum shell 10. Fins 40 may be provided on the acetabulum shell 10 to prevent rotation within the bone 14.

Figure 5:
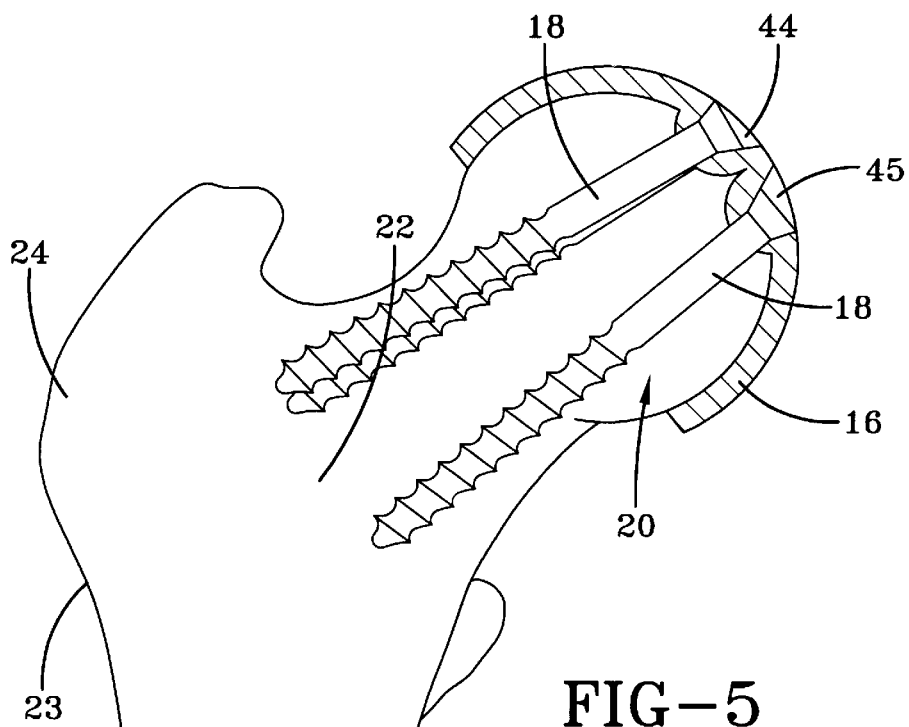
FIG. 5 shows an elevation view of an alternative embodiment of the cap secured on the femoral head (as it would be visible by x-ray through bone); and, FIG. 6 shows a plan view of the top of the cap of FIG. 5.
Figure 6:
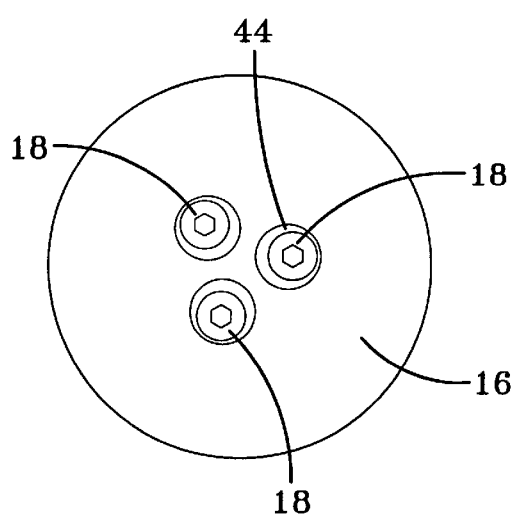

Other preferred features of the present invention include the screws 18, 12, 37 being cancellous screws installed in countersunk retrograde position. The screws may be positioned as shown or they may be installed in somewhat different positions as the surgeon believes best for any particular patient. The countersunk feature is best shown in FIG. 5 at areas 44, 45. One screw 18 may be all that is needed in a particular patient to hold the cap 16 in place, while in other patients multiple screws may be preferred. FIGS. 5 and 6 show a three-screw arrangement. By countersinking the screws 18 the screw heads do not rub against the interior surface 11 of the shell 10.

Figure 2:
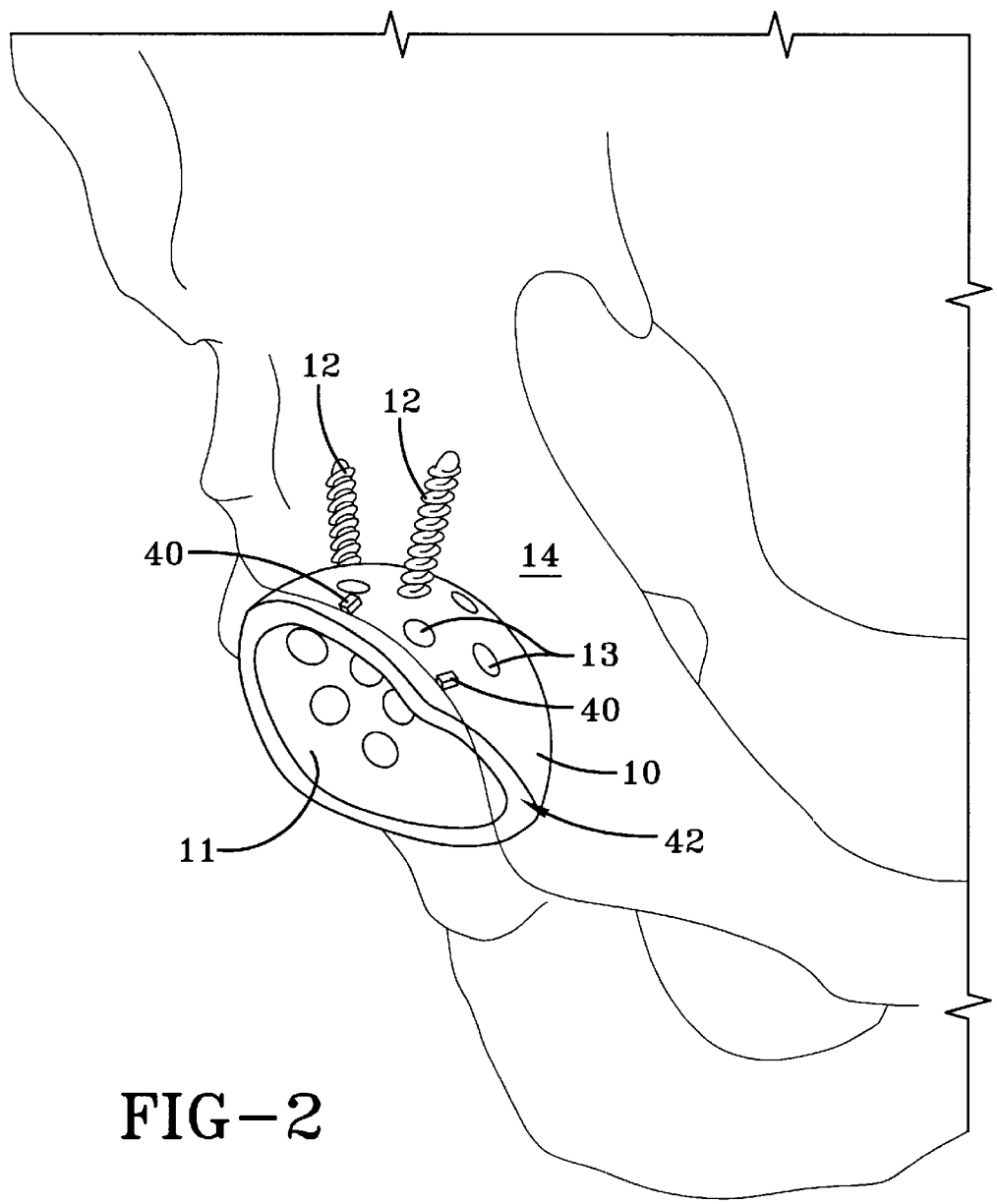
FIG. 2 is an elevation view of a preferred acetabulum shell of the present invention secured within the iliac fossa, (as it would be visible by x-ray through bone)
Figure 3:
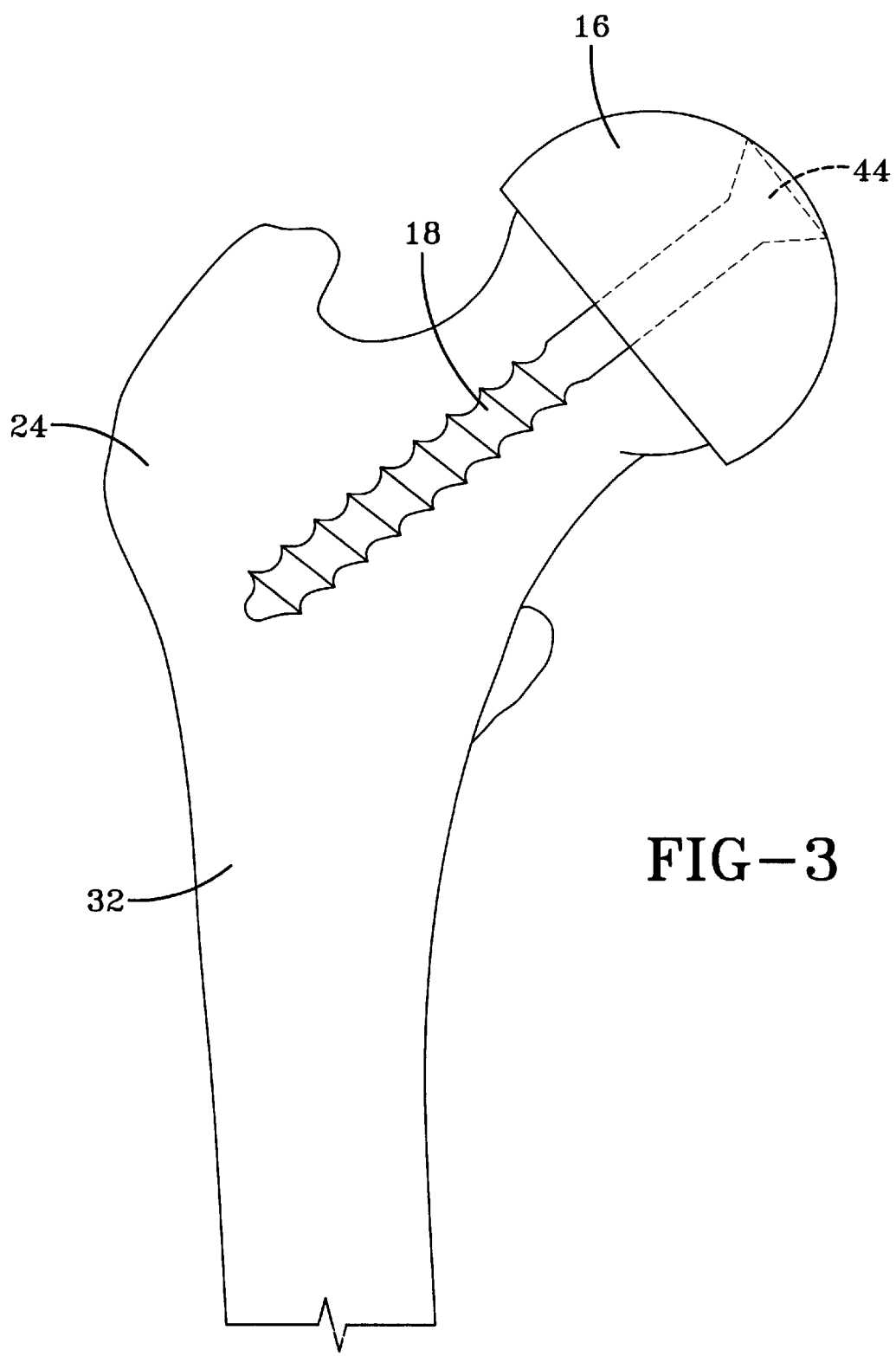
FIG. 3 is an elevation view of a cap of the present invention secured to the femoral head, (as it would be visible by x-ray through bone)
Figure 4:
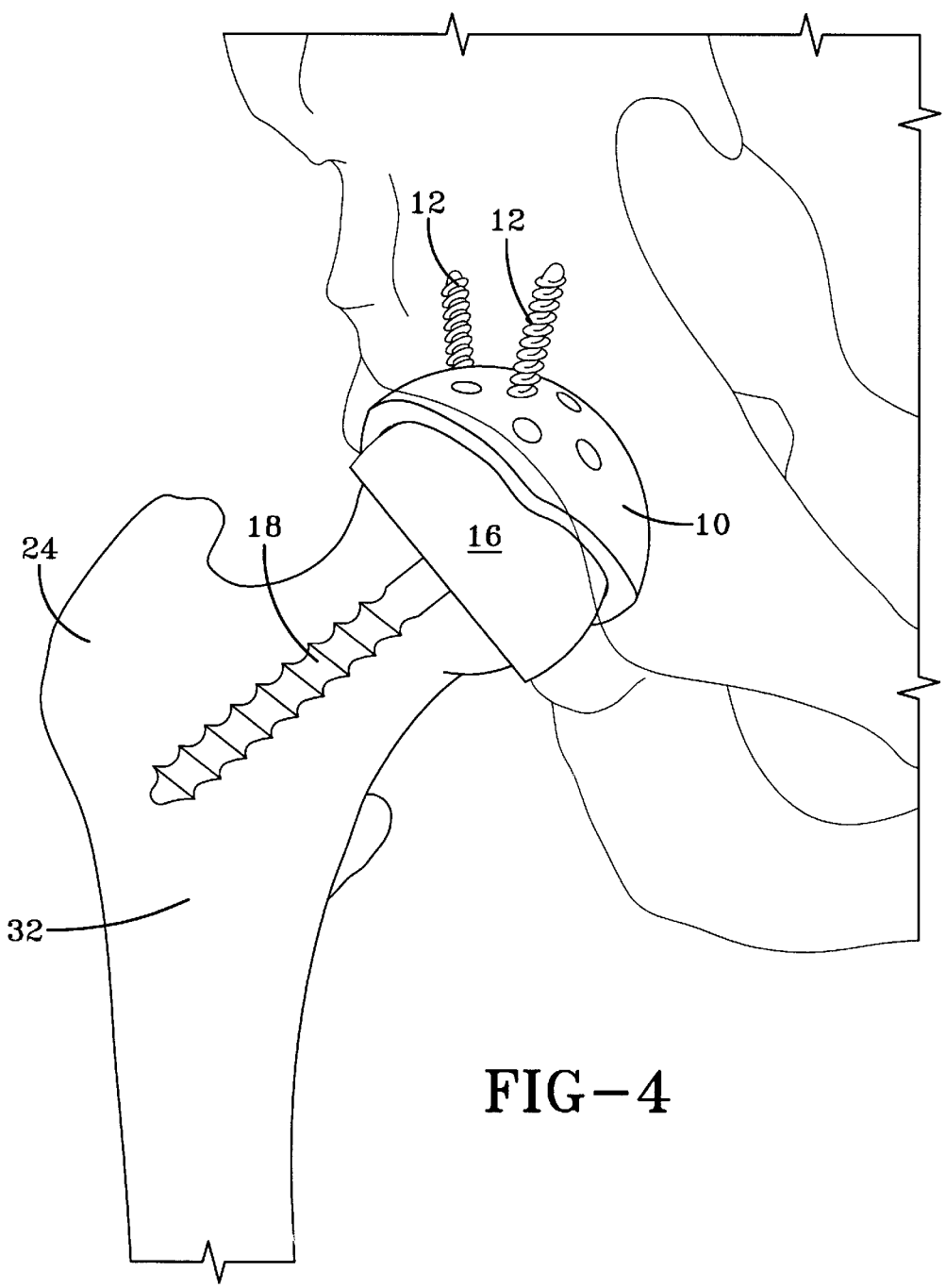
FIG. 4 is an elevation view of an assembled and installed cap and shell of the present invention secured to the femoral head and the iliac fossa respectively, (as it would be visible by x-ray through bone)

The acetabulum shell 10 may be provided with a psoas recess 42 as best shown in FIG. 2 to allow movement of the illio-psoas tendon without rubbing on the edge of the shell 10. The recess 42 is formed by a cutaway portion of the shell 10 that would otherwise continue the hemispherical shape of the shell. The shell has several apertures 13 to receive fasteners therethrough. Not all apertures require fasteners, but may nevertheless be provided to offer each surgeon flexibility on where and how many fasteners to install.

Figure 1A:
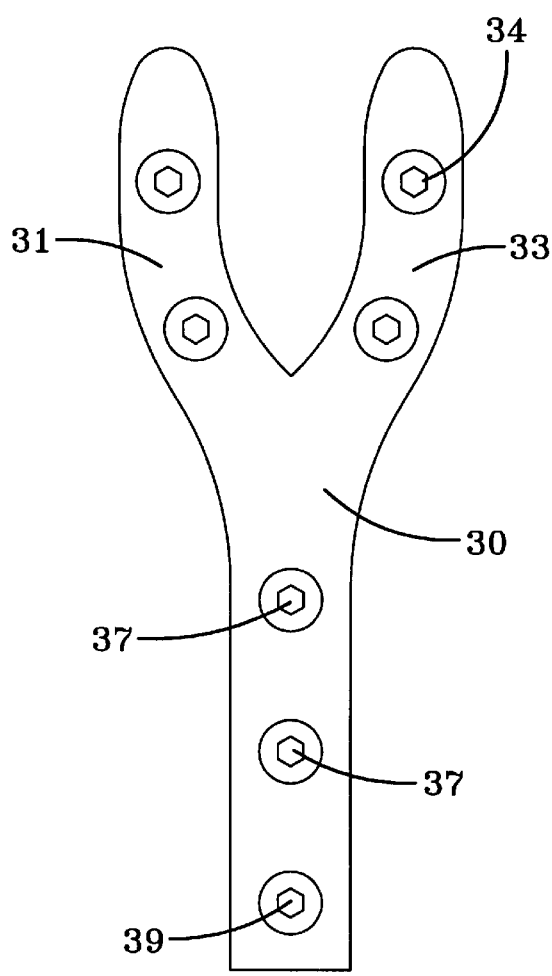
FIG. 1A is a plan view of a trochanteric osteotomy plate of a preferred embodiment of the present invention.
Figure 1B:
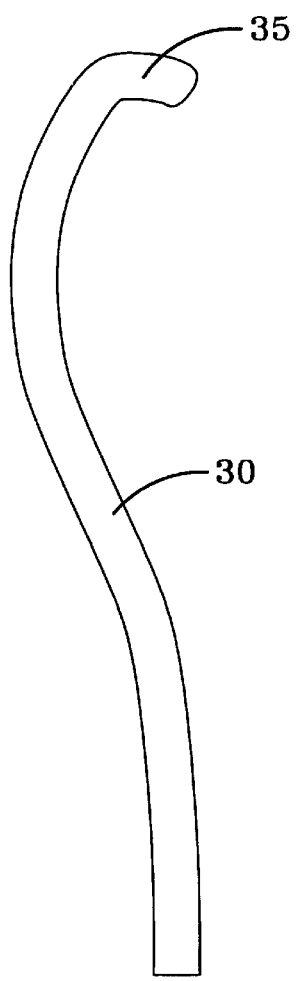
FIG. 1B is a side elevation view of the osteotomy plate of FIG. 1A.

The plate 30 may have branches 31, 34 as shown in FIG. 1A that curve over the greater trochanter as shown in FIG. 1B at 35. The screws 37 may also be retrograde, cancellous screws that install on either side of the screw 18 as shown in FIG. 1.

The cap 16 and shell 10 are preferably made of chrome-cobalt alloy metal, but may also be made of alternative bearing materials, such as titanium or plastics. The plate 30 is preferably made of chrome-cobalt alloy material but may also be made of alternative materials, including titanium, other metals and plastics. The screws are preferably made of chrome-cobalt alloy metal or other metal, or plastics, or biodegradable materials.

Additional advantages and modifications will be readily apparent to those skilled in the art. The present invention in its broadest aspects is, therefore, not limited to the specific details, exemplary apparatus and method and illustrative figures shown and described herein. Accordingly, departures may be made from such details without departing from the spirit or scope of Applicant's invention.

What is claimed is:

1. A total anatomic hip prosthesis, comprising:

a hemispherical prosthetic acetabulum shell adapted to be secured to an acetabulum bone;

a hemispherical cap adapted to be secured to a femoral head, and insertable into a cavity inside said acetabulum shell; and a trochanteric osteotomy plate in the shape of a "Y" that is adapted to be secured over the top of a greater trochanteric bone fragment and down along the lateral shaft of a femur wherein the trochanteric osteotomy plate is affixed with cancellous screws that pass through each arm of the "Y" and continue past an osteotomy and into the neck of the femur.

2. A total hip replacement assembly, comprising:

a femoral head cap component affixed to a prepared femur with at least one screw extending through and recessed with respect to the articular surface thereof;

an acetabulum shell affixed to an acetabulum with at least one screw extending through and recessed with respect to the articular surface thereof, and a trochanteric osteotomy plate in the shape of a "Y" that hooks over the top of a greater trochanteric bone fragment and extends down along the lateral shaft of a femur with screws that pass through each arm of the "Y".

3. The assembly of claim 2, wherein said cap and said shell are both made of metal, and contacting surfaces of each result in a metal on metal resurfacing hip replacement.

4. The assembly of claim 3, wherein said cap and said shell are both made of chrome-cobalt alloy metal.

* * * * *